United States Patent
Zickler et al.

(10) Patent No.: US 8,246,609 B2
(45) Date of Patent: Aug. 21, 2012

(54) INTRACORNEAL INLAY, SYSTEM, AND METHOD

(75) Inventors: Leander Zickler, Mountain View, CA (US); Scott J. Catlin, Orange, CA (US); Andrew Y Pang, Costa Mesa, CA (US)

(73) Assignee: AMO Development, LLC., Santa Ana, CA (US)

( * ) Notice: Subject to any disclaimer, the term of this patent is extended or adjusted under 35 U.S.C. 154(b) by 684 days.

(21) Appl. No.: 12/494,092

(22) Filed: Jun. 29, 2009

(65) Prior Publication Data

US 2009/0326650 A1    Dec. 31, 2009

Related U.S. Application Data

(60) Provisional application No. 61/076,592, filed on Jun. 27, 2008.

(51) Int. Cl.
*A61B 18/18* (2006.01)

(52) U.S. Cl. .................. 606/4; 606/11; 607/89; 128/898

(58) Field of Classification Search .................. 606/4, 5, 606/10–12; 607/88, 89; 623/4.1–5.16; 128/898
See application file for complete search history.

(56) References Cited

U.S. PATENT DOCUMENTS

| | | | |
|---|---|---|---|
| 4,646,720 A * | 3/1987 | Peyman et al. ............... | 128/897 |
| 4,764,930 A | 8/1988 | Bille et al. | |
| 5,312,428 A | 5/1994 | Lieberman | |
| 5,549,632 A | 8/1996 | Lai | |
| 5,993,438 A | 11/1999 | Juhasz et al. | |
| RE37,585 E | 3/2002 | Mourou et al. | |
| 6,949,093 B1 * | 9/2005 | Peyman ............................ | 606/5 |
| 7,044,602 B2 * | 5/2006 | Chernyak ....................... | 351/208 |
| 2001/0018612 A1 * | 8/2001 | Carson et al. ................ | 623/5.11 |
| 2004/0243111 A1 | 12/2004 | Bendett et al. | |
| 2006/0020259 A1 * | 1/2006 | Baumeister et al. ............. | 606/5 |
| 2006/0100612 A1 | 5/2006 | van der Heyd et al. | |
| 2006/0192921 A1 * | 8/2006 | Loesel et al. .................. | 351/219 |
| 2007/0208325 A1 | 9/2007 | Kurtz | |
| 2008/0262610 A1 * | 10/2008 | Lang et al. .................... | 623/5.16 |

FOREIGN PATENT DOCUMENTS

| | | |
|---|---|---|
| WO | 93/08878 A1 | 5/1993 |
| WO | 94/09849 A1 | 5/1994 |
| WO | 2006/011011 A1 | 2/2006 |
| WO | 2008/030699 A2 | 3/2008 |
| WO | 2008/060810 A2 | 5/2008 |
| WO | 2008/131888 A1 | 11/2008 |

* cited by examiner

*Primary Examiner* — Darryl J Collins
(74) *Attorney, Agent, or Firm* — AMO Development, LLC.

(57) ABSTRACT

Method and system for modifying a refractive profile associated with an eye having a recipient cornea. The method includes obtaining a corneal tissue inlay from a donor cornea, forming a recipient bed in the recipient cornea, and positioning the corneal tissue inlay into the recipient bed to correct the refractive profile of the eye with the refractive profile of the corneal tissue. The system includes a laser assembly outputting a pulsed laser beam, and a controller coupled to the laser assembly. The controller directs the laser assembly to incise a corneal tissue inlay from a donor cornea, form a recipient bed in the recipient cornea having a contour matching the contour of the inlay, register the inlay with the recipient bed, determine a position of the inlay, and determine a position change for the inlay based on the position of the inlay to align the refractive profile of the inlay with the refractive profile of the eye.

19 Claims, 4 Drawing Sheets

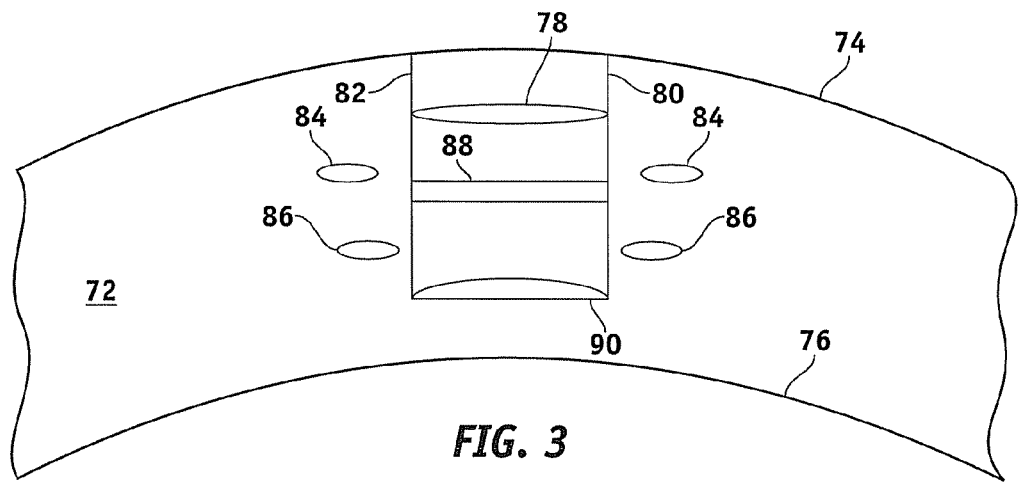
FIG. 3
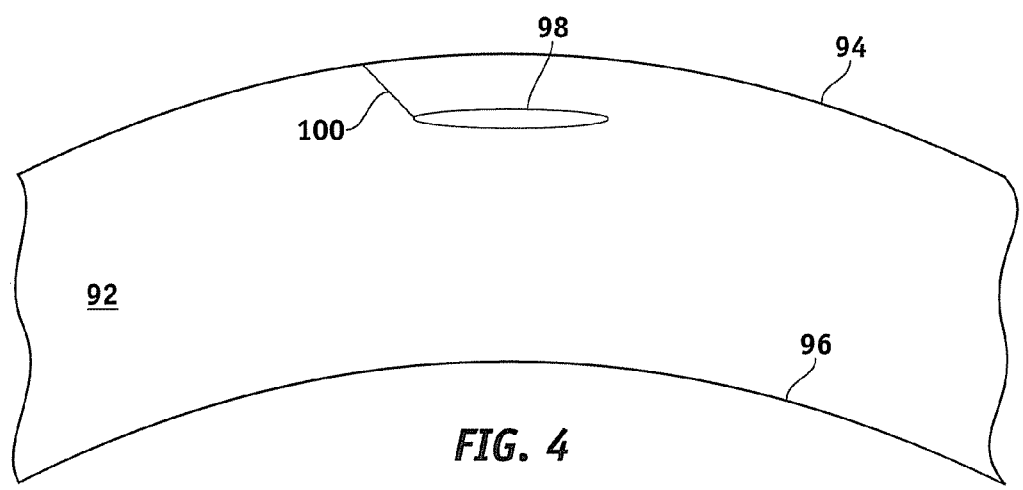
FIG. 4
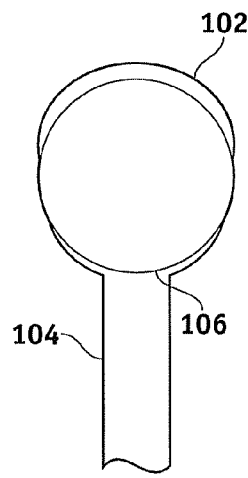 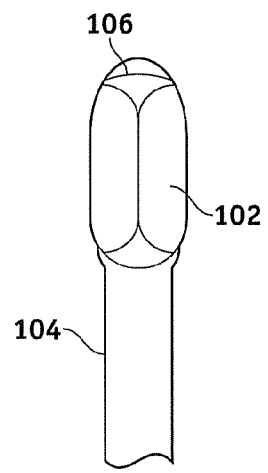
FIG. 5　　　　　　　　FIG. 6

INTRACORNEAL INLAY, SYSTEM, AND METHOD

CROSS-REFERENCE TO RELATED APPLICATION

This application claims the benefit of U.S. Provisional Application No. 61/076,592, filed Jun. 27, 2008.

BACKGROUND OF THE INVENTION

1. Field of the Invention

The field of the present invention is generally related to ophthalmic implants and more particularly, to systems and methods for correcting ophthalmic abnormalities of the eye using intracorneal inlays.

2. Background

Intracorneal implants (e.g., inlays) have been developed in an attempt to correct abnormalities of the eye. An intracorneal implant may be implanted or inserted into a desired region of the cornea, such as within the stroma of the cornea. In one technique, a stromal pocket is created by making an incision in the stromal layer of the cornea or by removing a small amount of stromal tissue during the implant procedure. The implant is typically placed in the stromal pocket to reshape the cornea, alter refractive properties of the cornea, or both. Some examples of clinical applications for corneal inlays include, but are not necessarily limited to, the treatment of thin corneas, ectasia, presbyopia, corneal damage, and the like.

Following implantation of some conventional corneal inlays, inflammation, cloudiness, deposits on or in the inlay, and/or deposits in the corneal tissue have been observed. These conventional corneal inlays, which are typically polymer-based, may interfere with nutrient and oxygen flow from the interior of the cornea through to the epithelium. Once implanted, conventional corneal inlays are generally difficult to remove, and in situ modification of corneal inlays may be also difficult.

Accordingly, it is desirable to provide systems and methods for correcting ophthalmic abnormalities of the eye that minimize the occurrence of one or more undesired corneal tissue responses (e.g., inflammation, cloudiness, inlay deposits, corneal tissue deposits, and the like). It is also desirable to provide systems and methods for correcting a refractive profile of the eye using an intracorneal inlay that allows proper nutrient/oxygen flow therethrough. It is also desirable to provide systems and methods for treating corneal thinning or damage (e.g., resulting from previous laser vision corrections or other ophthalmic surgical treatment), ectasia, presbyopia, and/or the like. It is also desirable to provide systems and methods for controlling the placement or positioning of an intracorneal inlay. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed to inlays and precisely positioning the inlays in a stable location within the cornea. In one embodiment, the inlay is formed from a donor cornea and modifies the refractive profile of an eye. This corneal tissue inlay may have a variety of shapes (e.g., lens based shapes, such as bi-convex, plano-convex, meniscus, and the like) and be configured with a variety of perimeter shapes (e.g., round, oval, polygonal, and the like). For example, a portion of corneal tissue may be incised from a donor cornea and modified (e.g., using a femtosecond laser, an excimer laser, or other surface or sub-surface photoaltering device) to form the corneal tissue inlay.

In one embodiment, a method is provided for modifying a refractive profile associated with an eye having a recipient cornea. The method includes obtaining a corneal tissue inlay from a donor cornea, forming a recipient in the recipient cornea, and positioning the corneal tissue inlay into the recipient bed. The corneal tissue inlay has a refractive profile, and the refractive profile of the eye is altered by the refractive profile of the corneal tissue inlay.

In another embodiment, system is provided for modifying the refractive profile associated with the eye. The system includes a laser assembly operable to output a pulsed laser beam and a controller coupled to the laser assembly. The controller directs the laser assembly to incise a corneal tissue inlay from a donor cornea, form a recipient bed in the recipient cornea, register the corneal tissue inlay with the recipient bed, determine a position of the corneal tissue inlay, and determine a position change for the corneal tissue inlay based on the position of the corneal tissue inlay to align the refractive profile of the corneal tissue inlay with the refractive profile of the eye. The corneal tissue inlay has a refractive profile correcting for the refractive profile of the eye, and the recipient bed has a contour matching a contour of the corneal tissue inlay.

In yet another embodiment, the system includes a user interface operable to display an image of the eye, a laser assembly operable to output a pulsed laser beam, and a controller coupled to the laser assembly and the user interface. The controller directs the laser assembly to incise a corneal tissue inlay from a donor cornea, form a recipient bed in the recipient cornea, determine a position of the corneal tissue inlay, and determine an error signal for the corneal tissue inlay based on the position of the corneal tissue inlay to align the refractive profile of the corneal tissue inlay with the refractive profile of the eye, the error signal indicated on the image of the eye. The corneal tissue inlay has a refractive profile correcting for the refractive profile of the eye, and the recipient bed has a contour matching a contour of the corneal tissue inlay.

BRIEF DESCRIPTION OF THE DRAWINGS

In the drawings, wherein like reference numerals refer to similar components:

FIG. 3 is a cross-sectional view of a donor cornea illustrating the formation of some corneal tissue inlays;

FIG. 4 is a cross-sectional view of a recipient cornea illustrating pocket formation;

FIG. 5 is a top view of a corneal tissue inlay and a portion of an inserter in accordance with one embodiment;

FIG. 6 is a top view of the corneal tissue inlay and the inserter shown in FIG. 5 illustrating an insertion mode in accordance with one embodiment.

DETAILED DESCRIPTION

Figure 1:
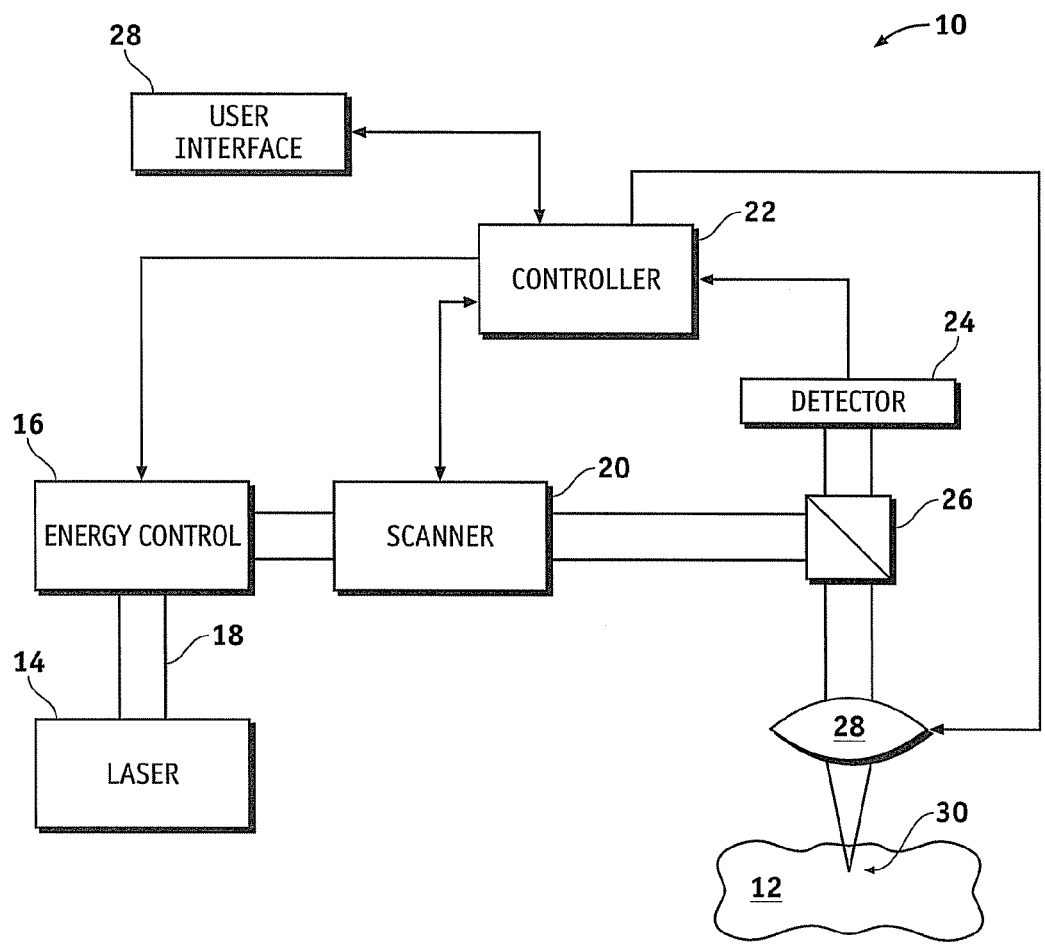
FIG. 1 is a block diagram of an ophthalmic laser system in accordance with one embodiment of the present invention.

The present invention provides systems and methods for forming a corneal implant or inlay from a donor corneal tissue (e.g., a cadaver cornea or the like). The corneal tissue inlay may have a variety of shapes. For example, from a side perspective (e.g., a cross-sectional view, a side profile, or the like), the corneal tissue inlay may be lens-shaped (e.g., bi-convex, plano-convex, meniscus, and the like) or any other suitable shape including, but not necessarily limited to, a rectangular shape or a polygonal shape. From along an optical axis perspective, the corneal tissue inlay may have any suitable shape (e.g., round, oval, polygonal, or the like). Additionally, the corneal tissue inlay may have an edge that is configured to stabilize the location of the corneal tissue inlay within a recipient cornea. For example, the edge of the corneal tissue inlay may be shaped (e.g., top-hat shaped, zig-zag shaped, and the like) to hold the inlay in place within the recipient cornea. After the inlay has been shaped and removed from the donor cornea, or vice versa, the inlay is implanted into the recipient cornea. The systems for forming the corneal implant can also form a recipient bed in the recipient cornea preferably with a contour matching the contour of the corneal implant.

In one embodiment, the method includes incising a portion (e.g., a lenticule) of the donor cornea (e.g., using a femtosecond laser) to form the corneal tissue inlay, removing the inlay from the donor cornea, creating a substantially matching pocket having an access (e.g., with a femtosecond laser) in the recipient cornea, and inserting the corneal tissue inlay into the recipient pocket. For example, a portion of corneal tissue may be incised from a cadaver cornea with a femtosecond laser beam and removed from the cadaver cornea. The inlay may also be modified after removal from the donor cornea and prior to insertion into the recipient cornea. A refractive profile may be determined for the extracted portion of corneal tissue, and this refractive profile can be altered with a laser beam to produce the corneal inlay. For example, the inlay may be photoaltered (e.g., surface re-shaping via a femtosecond laser and/or an excimer laser), chemically modified (e.g., by application of nutrient solution to enhance corneal tissue cross-linking, biomechanical properties, and/or healing), mechanically modified (e.g., via cryogenic lathing), any combination of the foregoing modifications, or the like. With proper tissue matching, implanted or inserted corneal tissue inlays generally avoid many of the undesired tissue reactions normally associated with conventional corneal inlays (i.e., polymer based inlays or non-biological based inlays), such as inflammation, cloudiness, inlay deposits, corneal tissue deposits, and the like. For example, corneal tissue inlays allow nutrient/oxygen transfer through the inlay to avoid much, if not all, of the undesired tissue reactions associated with conventional corneal inlays that lack nutrient/oxygen transfer capability or have substantially limited capabilities thereof.

Referring to the drawings, an ophthalmic laser system 10 is shown in FIG. 1. The system 10 includes, but is not necessarily limited to, a laser source 14 capable of generating a pulsed laser beam 18, an energy control module 16 for varying the pulse energy of the pulsed laser beam 18, a scanner 20, a controller 22, a user interface 28, and focusing optics 28 that direct one or more focal points 30 of the pulsed laser beam 18 onto the surface of or within the eye 12 (e.g., sub-surface into the corneal region, such as sub-epithelium, sub-Bowman's layer, within the stroma, substantially adjacent to Descemet's membrane, and the like). The laser source 14, energy control module 16, scanner 20, and focusing optics 28 collectively form a laser assembly. The controller 22 (e.g., a processor operating suitable control software) communicates with one or more of the scanner 20, user interface 28, and focusing optics 28 to control the direction of the focal point 30 as it is scanned along the desired region of the eye 12 and thereby directs the laser assembly during operation. The user interface 28 provides the user with a variety of input parameters for controlling the system 10. For example, the pulsed laser beam 18 may be controlled based on one or more input parameters to produce a desired incision. In one embodiment, the user interface 28 determines the type of corneal implant to be used for a particular ophthalmic procedure. Based on this determination, the controller 22 automatically configures the system 10 to a set of pre-determined operating values corresponding with the specific corneal implant. For customization (e.g., patient specific factors, historical performance, and the like), the user may modify one or more of these operating values via the user interface 28.

In one embodiment, software, firmware, or the like, can be used (executed by the controller 22 to control or direct one or more components of the system 10) to command the actions and placement of the scanner via a motion control system, such as a closed-loop proportional integral derivative (PID) control system. In this embodiment, the system 10 further includes a beam splitter 26 and a detector 24 coupled to the controller 22 to provide a feedback control mechanism for the pulsed laser beam 18. The beam splitter 26 and detector 24 may also be omitted in other embodiments, for example, with different control mechanisms.

Movement of the focal point 30 of the pulsed laser beam 18 is accomplished via the scanner 20 in response to the controller 22. In one embodiment, the scanner 20 scans the pulsed laser beam 18 to produce an incision in the desired region of the cornea via photoalteration. In general, photoalteration of a material may be accomplished using a pulsed laser beam that is directed (e.g., via the scanner 20) at a desired region of the material. For example, a pulsed laser beam may be controlled to scan the desired region (e.g., on the surface or sub-surface) and to create a separation of the material (e.g., which may be used to produce a flap of the material, to separate a portion of the material for transplants or implants, to create a receptacle or pocket for receiving implants, inlays or onlays, or for a variety of other uses). Typically, a pulsed laser beam is focused onto a desired area of the material to photoalter the material in this area and, in some instances, the associated peripheral area. Examples of photoalteration of the material include, but are not necessarily limited to, chemical and physical alterations, chemical and physical breakdown, disintegration, ablation, vaporization, or the like. For example, the pulsed laser beam may also be used to sculpt an external surface or a sub-surface layer (e.g., to impart a desired or pre-determined refractive or diffractive profile and the like). Although various embodiments of systems, graphical user interfaces, and methods for ophthalmic surgery are described, these systems, graphical user interfaces, and methods may be applied to other biological tissues and other materials.

One example of photoalteration using pulsed laser beams is the photodisruption (e.g., via laser induced optical breakdown) of a material. Localized photodisruptions can be placed at or below the surface of the material to produce high-precision material processing. For example, a micro-optics scanning system may be used to scan the pulsed laser beams to produce an incision in the material and create a flap, a pocket, or a cavity therefrom. The term "scan" or "scanning" refers to the movement of the focal point of the pulsed laser beam along a desired path (e.g., along an x-axis, a y-axis, a z-axis, or any combination thereof) or in a desired pattern.

To provide the pulsed laser beam 18, a chirped pulse laser amplification system, such as described in U.S. Pat. No. RE37,585, may be used for photoalteration. U.S. Pat. Publication No. 2004/0243111 also describes other methods of photoalteration. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

In this case, the focusing optics 28 direct the pulsed laser beam 18 toward a region 12 of the eye (e.g., onto the cornea) for plasma mediated (e.g., non-UV) photoablation of superficial tissue on the eye, or into the stroma for intrastromal photodisruption of tissue. The system 10 is capable of generating the pulsed laser beam 18 with physical characteristics similar to those of the laser beams generated by a laser system disclosed in U.S. Pat. Nos. 4,764,930 and 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue. The wavelength of the pulsed laser beam 18 is generally in the range of about 3 μm to about 1.9 nm, and preferably between about 400 nm to about 3000 nm. For accomplishing photodisruption of stromal tissues at the focal point, the irradiance of the pulsed laser beam 18 is preferably greater than the threshold for optical breakdown of the tissue. Although a non-UV, ultrashort pulsed laser beam is described in this embodiment, the pulsed laser beam 18 may have other pulse durations and different wavelengths in other embodiments (e.g., UV wavelengths for excimer applications and the like).

Scanning is accomplished with the scanner 20 via the controller 22 by selectively moving the focal point(s) 30 to produce a structured scan pattern (e.g., a raster pattern, a spiral pattern, or the like) of scan spots. Operating the scanner 20 to scan this structured pattern is particularly useful for controlling the spacing between scan spots of the pattern. The step rate at which the focal point 30 is moved is referred to herein as the scan rate. For example, the scanner 20 can operate at scan rates between about 10 kHz and about 400 kHz, or at any other desired scan rate. In one embodiment, the scanner 20 generally moves the focal point of the pulsed laser beam 18 through the desired scan pattern at a substantially constant scan rate while maintaining a substantially constant separation between adjacent focal points. Further details of laser scanners are known in the art, such as described, for example, in U.S. Pat. No. 5,549,632, the entire disclosure of which is incorporated herein by reference.

In one embodiment, the scanner 20 includes, but is not necessarily limited to, a pair of scanning mirrors or other optics (not shown) to angularly deflect and scan input beam (e.g, the pulsed laser beam 18). For example, scanning mirrors driven by galvanometers may be employed where each of the mirrors scans along different orthogonal axes (e.g., an x-axis and a y-axis). A focusing objective (not shown), having one or more lenses, images the input beam onto a focal plane of the system 10. The focal point 30 may thus be scanned in two dimensions (e.g., along the x-axis and the y-axis) within the focal plane of the system 10. Scanning along the third dimension, i.e., moving the focal plane along an optical axis (e.g., a z-axis), may be achieved by moving the focusing objective, or one or more lenses within the focusing objective, along the optical axis. Thus, a variety of incisions, sculpting, areas, volumes, and the like may be accomplished by varying the position of the focal point 30 along one or more of these axes while scanning.

For ophthalmic applications (e.g., preparing a cornea for flap separation, lenticule incision, corneal transplant, preparing a pocket or cavity in the cornea, or the like), an area (e.g., substantially circular, oval, or other shape) may be scanned with a scan pattern based on the movement of the scanning mirrors. As the focal point 30 is scanned along a corneal bed, the pulsed laser beam 18 photoalters the stromal tissue. Using structured patterns, the distribution of scan spots is generally determined by the pulse frequency, the scan rate, and the amount of scan line separation. Generally, higher scan rates, enable shorter procedure times by increasing the rate at which corneal tissue can be photoaltered. For example, the scan rates may be selected from a range between about 30 MHz and about 1 GHz with a pulse width in a range between about 300 picoseconds and about 10 femtoseconds, although other scan rates and pulse widths may be used.

The controller 22 includes computer hardware and/or software, often including one or more programmable processing units operable to execute machine readable program instructions or code for implementing some or all of one or more of the methods described herein. The code is often embodied in a tangible media such as a memory (optionally a read only memory, a random access memory, a non-volatile memory, or the like) and/or a recording media (such as a floppy disk, a hard drive, a compact disc, a digital video disc, a flash memory, a memory stick, or the like). The code and/or associated data and signals may also be transmitted to or from the controller 22 via a network connection (such as a wireless network, an Ethernet, the Internet, an intranet, or the like) to the system 10, and some or all of the code may also be transmitted between components of the system 10 and/or within the controller 22 via one or more bus, and appropriate standard or proprietary communications cards, connectors, cables, and the like will often be included in the controller 22. The controller 22 is often configured to perform the calculations and signal transmission steps described herein at least in part by programming the controller with the software code, which may be written as a single program, a series of separate subroutines or related programs, or the like. The controller 22 may include standard or proprietary digital and/or analog signal processing hardware, software, and/or firmware, and will typically have sufficient processing power to perform the calculations described herein during treatment of the patient. The controller 22 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with computer systems may also be included, and processors having a plurality of processing units (or even separate computers) may be employed in a wide range of centralized or distributed data processing architectures.

A database is stored in a memory accessible by the controller 22, within the controller 22, or using a combination thereof. The database includes a catalogue of incisions, combinations of incisions, and ablation patterns that can be retrieved for forming a variety of corneal tissue inlays, recipient beds, and other corneal-based structures for receiving the inlay. Some examples of corneal tissue inlay types include, but are not necessarily limited to, a variety of discs with varying radii of curvatures associated with the anterior and/or posterior surfaces of the disc and/or with varying cross-sectional shapes, single or multi-perforated discs, multi-component implants, crescents, rings, lenses, and the like. Additional corneal tissue inlay types may be derived from variants of these examples based on pre-determined sizes or dimensions. To accommodate the variety of inlay types and specification, some inlay parameters that may be included in the database include, but are not necessarily limited to, sub-surface depth, shape, size, diameter, thickness, radii, edge type, surface contour, cross-sectional profile, perimeter profile, and the like. The dimensions of a corneal tissue inlay type may be used to pre-program incision parameters (e.g., length, depth, volume, shape, and the like), incision combinations, and/or ablation patterns. Pre-programmed instructions for controlling the laser assembly may also be stored in the memory database for retrieval by the controller 22 to direct the laser assembly in producing the desired incision or ablation. These instructions, as well as the catalogue of incisions, combinations of incisions, ablation patterns, inlay parameters, and incision parameters, may be updateable (e.g., via input port or memory read device of the user interface 28) are thus available to the system 10 for incising the desired corneal tissue inlay from a donor cornea and for forming the appropriate incision, cavity (e.g., a pocket), or recipient bed in the recipient cornea to receive the corresponding corneal tissue inlay.

In one embodiment, the database further includes information pertaining to corneal tissue re-shaping in response to a variety of factors (e.g., patient age, corneal characteristics, pre-procedure refractive conditions associated with the patient, or the like). This information may also be historically observed and accumulated from one or more patients or patient populations and stored in the database. Using operator input or controller 22 selection based on operator specified criteria (e.g., associated with the patient), one or more instruction sets can be selected and retrieved by the controller 22 to direct the operation of the laser assembly. The instruction set may also be modified by the operator (e.g., physician) to customize the corneal tissue inlay and/or recipient bed. Additionally, the incision type or pattern or ablation pattern may be wholly specified by the operator apart from the instruction sets stored in the database. The database can also be periodically updated, such as by a network connection to a central database, system software upgrades, or the like.

The system 10 may additionally acquire detailed information about optical aberrations to be corrected, at least in part, using the system 10. Examples of such detailed information include, but are not necessarily limited to, the extent of the desired correction, and the location in the cornea of the eye associated with the correction (e.g., where the correction can be made most effectively). The refractive power of the cornea may be used to indicate corrections. Wavefront analysis techniques, made possible by devices such as a Hartmann-Shack type sensor (not shown), can be used to generate maps of corneal refractive power. Other wavefront analysis techniques and sensors may also be used (e.g., based on phase diversity or other techniques). The maps of corneal refractive power, or similar refractive power information provided by other means, such as corneal topographs or the like, can then be used to identify and locate the optical aberrations of the cornea that require correction. Optical aberration information acquired by other methods may also be utilized with the system 10, such as imaging techniques using optical coherence tomography (OCT) or other interferometric imaging schemes. In one embodiment, the user interface 28 includes one or more input ports for receiving optical aberration data, treatment planning based on such optical aberration data, wavefront analysis data, topographic data, pachymetry data, or the like. For example, the input port may be a networking port (e.g., local area network, wide area network), a bus connection (e.g., universal serial bus port), wireless transceiver (e.g., WiFi, Bluetooth, or the like), or the like, configured to couple a media read device, the Internet, an intranet, or external data resource. In another embodiment, the user interface 28 includes a media read device, such as a flash memory drive, digital video disc drive, compact disc drive, optical disc drive, or the like, that transfers the aforementioned data from a corresponding data storage medium to the system 10.

In general, when the laser source 14 is activated, the focal spot 30 is selectively directed (e.g., via the scanner 20) along a beam path to photoalter stromal tissue. For example, the focal spot 30 is moved along a predetermined length of the beam path in one reference area. The pulsed laser beam 18 is then redirected through another reference area, and the process of photoalteration is repeated. The sequence for directing the pulsed laser beam 18 through individually selected reference areas can be varied, and the extent of stromal tissue photoalteration while the incising laser beam is so directed, can be varied. Specifically, as indicated above, the amount of photoalteration can be based on the refractive power map. On the other hand, the sequence of reference areas that is followed during a customized procedure will depend on the particular objectives of the procedure.

The scanner 20 may also scan a predetermined pattern using one or more scan patterns to one or more combinations of these reference areas or scan a single line (e.g., to produce a sidecut or continuous incision). One example of an ophthalmic scanning application is the creation of a cavity or a pocket in the cornea. The laser focal spot 30 of the pulsed laser beam 18 may be scanned at a pre-determined subsurface depth of the cornea (e.g., such as sub-epithelium, sub-Bowman's layer, within the stroma, substantially adjacent to Descemet's membrane, and the like) to form a pocket bed. An incision may be made to connect the surface of the eye with the pocket bed to form an access to the pocket. The desired corneal implant, or specific component of a multi-component corneal implant, is then inserted through this incision. Although a single incision is described in this embodiment, additional incisions may be made to connect the surface of the eye with the pocket bed.

In another embodiment, intrastromal tissue is photoaltered by the system 10 (e.g., incised) so as to create an isolated lenticule of intrastromal tissue, and the lenticule of tissue can then be removed from the cornea (e.g., through an incision). Other shapes, volumes, or portions of corneal tissue may be also be isolated by selective incisions (e.g., for use as a corneal tissue inlay). The incision selection may be based at least in part on the alteration of the shape of a recipient cornea as particular to the vision correction procedure, a desired refractive or diffractive affect, and the like. To maximize the utility of a donor cornea, several lenticules may be incised from the donor cornea. One benefit of the system 10 allows multiple corneal tissue inlays to be harvested from a single donor cornea.

Each corneal tissue implant may also be modified following removal from the donor cornea. For example, the pulsed laser beam 18 may be scanned along a surface of the lenticule (e.g., an anterior surface or a posterior surface based on the orientation of the lenticule after insertion or implantation into the recipient cornea). In another embodiment, a laser beam from an excimer laser (not shown) may be used to photoalter one or more surfaces of the lenticule after removal from the donor cornea (e.g., to create the desired refractive or diffractive properties of the resulting corneal tissue inlay by contouring the anterior and/or posterior surface of the lenticule).

Figure 2:
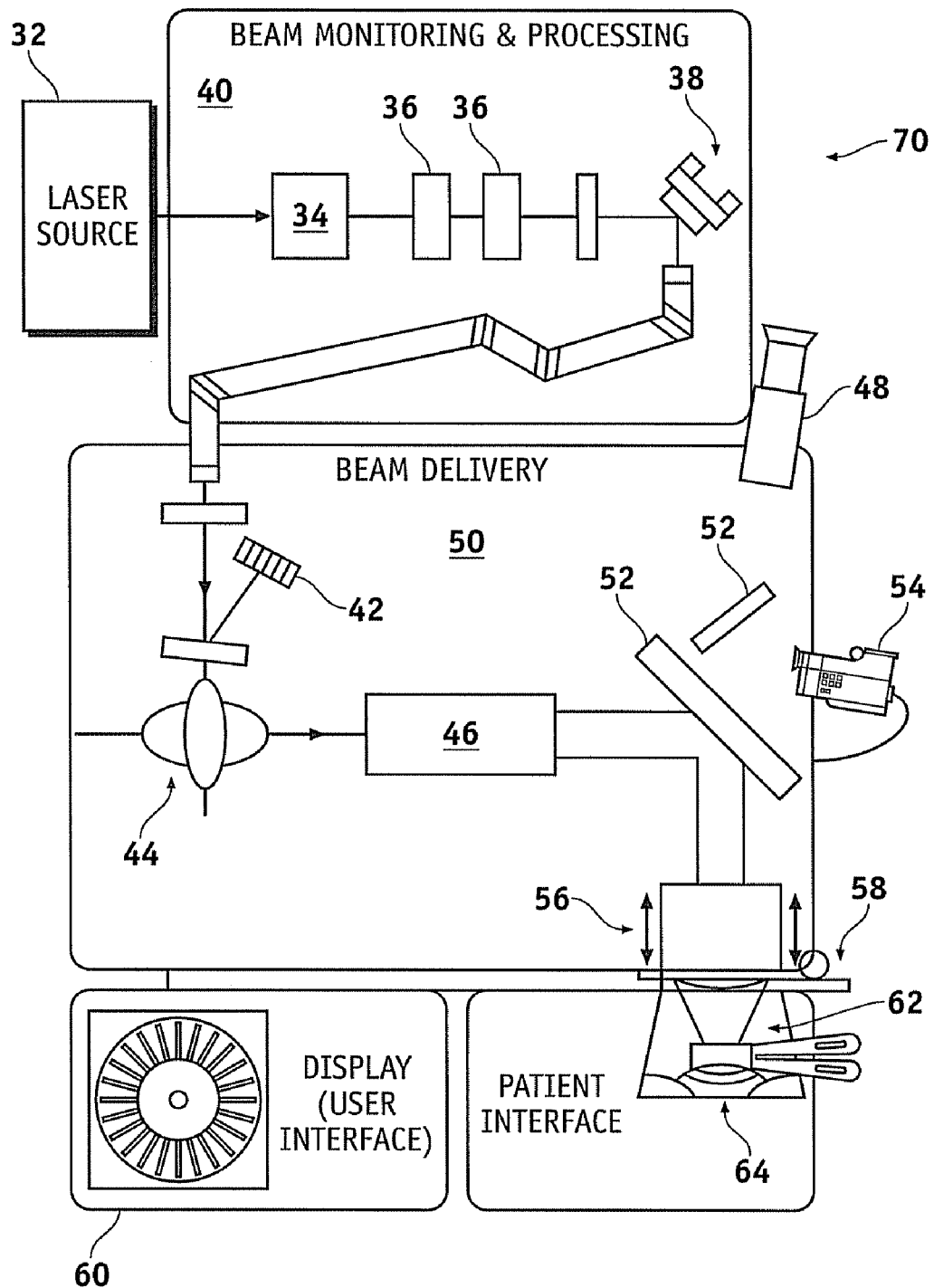
FIG. 2 is a schematic diagram of an ophthalmic laser system in accordance with another embodiment.

FIG. 2 is a block diagram of an ophthalmic laser system 70 in accordance with another embodiment of the present invention. The ophthalmic laser system 70 illustrates the optical path of the pulsed laser beam in greater detail and includes, but is not necessarily limited to, a laser source 32 providing a pulsed laser beam (e.g. from the laser 14 shown in FIG. 1), a beam monitoring and processing module 40, a beam delivery module 50, and a user interface 60. In this embodiment, the laser source 32, beam monitoring and processing module 40, and beam delivery module 50 collectively form a laser assembly. The pulsed laser beam is supplied to the beam monitoring and processing module 40 where operating characteristics of the pulsed laser beam are controlled, such as the pulse energy (e.g., varied by the energy control module 16 shown in FIG. 1), a focal point separation, a minimum sub-surface depth of the pulsed laser beam, and the like). The beam delivery module 50 scans the pulsed laser beam along a desired scan region. In this embodiment, the ophthalmic laser system 70 can be coupled to an eye 64 via a patient interface 62, and the patient interface 62 may be coupled to the ophthalmic laser system 70 at a loading deck 58, for example. A display is provided by the user interface 60 for viewing the eye 64 undergoing laser treatment.

In one embodiment, the beam monitoring and processing module 40 includes, but is not necessarily limited to, an energy attenuator 34, one or more energy monitors 36, and an active beam positioning mirror 38. The pulsed laser beam is directed from the laser source 32 to the energy attenuator 34, then to the energy monitor 36, and then to the active beam positioning mirror 38. The active beam positioning mirror 38 directs the pulsed laser beam from the beam monitoring and processing module 40 to the beam delivery module 50. Using the energy attenuator 34 and energy monitor 36, the pulse energy of the pulsed laser beam may be varied to desired values. Additionally, the spatial separation of the focal points of the pulsed laser beam may be varied by the beam monitoring and processing module 40.

The beam delivery module 50 scans the pulsed laser beam at the desired scan region (e.g., a sub-surface region of the eye 64, such as within the corneal epithelium and on or within Bowman's layer, the stroma, Descemet's membrane, the endothelium, and the like). In one embodiment, the beam delivery module 50 includes, but is not necessarily limited to, a beam position monitor 42, an x-y scanner 44 (e.g., such as the scanner 20 shown in FIG. 1), a beam expander 46, one or more beam splitters 52, and a z-scanning objective 56. In this embodiment, the beam delivery module 50 additionally includes an operating microscope 48 and a video camera 54 to enhance viewing of the eye 64.

The pulsed laser beam is received from the beam monitoring and processing module 40 by the x-y scanner 44 and directed to the beam expander 46, and the beam expander 46 directs the pulsed laser beam to the z-scanning objective via the beam splitter(s) 52. The z-scanning objective 56 can vary the focal point depth of the pulsed laser beam. For example, the z-scanning objective 56 can vary the focal point depth to the minimum focal point depth determined for the eye 64 or the desired region of the eye 64 and for the selected operating pulse energy and operating focal point separation.

The configuration of the ophthalmic laser system 70 may vary as well as the organization of the various components and sub-components of the ophthalmic laser system 70. For example, some sub-components of the beam delivery module 50 may be incorporated with the beam monitoring and processing module 40 and vice versa.

For corneal inlay or implant applications, the user interface 60 presents a variety of corneal implant options for selection by the user. In one embodiment, the user interface 60 includes, but is not necessarily limited to, a display and an input device, such as a touch-screen, a mouse, a keyboard, a touch-pad, or the like. Multiple images representing different types of corneal tissue implants are presented on the display, and the user may select the appropriate corneal tissue implant for a particular ophthalmic procedure. For example, the user may indicate a corneal tissue implant selection by touching the image on the touch-screen corresponding with the appropriate corneal implant. Some examples of corneal tissue implant types include, but are not necessarily limited to, a variety of discs with varying radii of curvatures associated with the anterior and/or posterior surfaces of the disc and/or with varying cross-sectional shapes, single or multi-perforated discs, multi-component implants, crescents, rings, lenses, and the like. Additional corneal tissue implant types may be derived from variants of these examples based on pre-determined sizes or dimensions.

Each corneal tissue implant type is associated with one or more parameters which may be selected or modified by the user (e.g., sub-surface depth, shape, size, diameter, thickness, radii, edge type, surface contour, cross-sectional profile, perimeter profile, and the like). The dimensions of a corneal tissue implant type may be used to pre-program incision parameters (e.g., length, depth, volume, shape, and the like) to be produced by the incision procedure. For each corneal tissue implant type, the system 10, 70 can form a corresponding incision or pocket in the recipient cornea. Pre-programmed (e.g., stored in the memory database accessible by the controller 22) and updateable incisions (e.g., via the input port or memory read device of the user interface 28, 60) are thus available to the system 10, 70 for incising a desired corneal tissue implant (e.g., lens shaped type, such as biconvex, plano-convex, multifocal, aspheric, and the like, polygonal shaped type, and the like) from the donor cornea and for forming the appropriate incision or cavity (e.g., a pocket) or stromal bed in the recipient cornea to receive the corresponding corneal tissue implant.

Once the corneal tissue implant parameters are selected or entered via the user interface 60, this data is provided to the controller 22 (FIG. 1). The controller 22 selects a pre-determined procedure (e.g., incision types and sequence), corresponding with the corneal tissue implant parameters, from among a stored database of pre-determined procedures and can modify the procedure to correspond with the corneal tissue implant parameters.

In one embodiment, the system 10, 70 includes a memory having a database. The memory stores an operating system module and a graphical user interface (GUI) module. The operating system module may include executable instructions for handling various system services, such as file services or for performing hardware dependant tasks. The GUI module may rely upon standard techniques to produce graphical components on the user interface 60, e.g., windows, icons, buttons, menus, drop-down menus, and the like, examples of which are discussed below. The GUI module may include executable instructions to receive input from a pointer device (e.g., a mouse, a keyboard, a touch-pad, and the like) or touch-screen and display a cursor on the user interface 60. Additionally, the GUI module includes executable instructions for selecting items in the GUI and image processing of the eye and implant position within the eye. The executable modules stored in memory are exemplary. It should be appreciated that the functions of the modules may be combined or divided into additional modules.

The database includes a catalog of corneal tissue implant types and a catalog of pre-determined incision procedures. Although described with catalogs, the database may be implemented with one or more look-up tables or other data management configurations. Each of the incision procedures corresponds to a different corneal tissue implant type, and the catalogs may be periodically updated.

The incision procedures are designated for association with the corresponding corneal tissue implant type, although a particular incision procedure may be applicable to more than one of the corneal tissue implant types. Some examples of corneal implant types include, but are not necessarily limited to, a variety of discs with varying radii of curvatures associated with the anterior and/or posterior surfaces of the disc and/or with varying cross-sectional shapes, single or multi-perforated discs, multi-component implants, crescents, rings, lenses, and the like. Additional corneal tissue implant types may be derived from variants of these examples based on pre-determined sizes or dimensions. Combinations of corneal tissue implant types and incisions to provide refractive corrections may also be cataloged.

In one embodiment, at least some of the incision parameters are presented on the user interface 60 and may be modified by the user. For example, drop-down menus, input blocks, incremental blocks, and the like may be used to set or modify one or more incision parameters (e.g., default incision parameter settings), the number and/or type of incisions, and the like associated with the particular incision procedure. Wavefront analysis, OCT maps, pupil dynamics (e.g., to assist with centration, incision selection, and/or implant selection), centration, iris registration, and the like, may also be used to determine incision parameters.

The system 10, 70 can determine a proper positioning or placement of the corneal tissue implant. One technique implemented by the system 10, 70 includes a shape registration, a feature registration, and iterative positioning using a closed loop feedback method. The shape registration refers to matching contours of the corneal tissue implant with the recipient bed (or pocket) to register the implant with an optical axis of the recipient's eye and enhance positional stability of the implant. For example, some portions or all of the contour and/or one or more external structural features of the implant are formed in the recipient bed such that the implant is aligned with the optical axis following insertion. Some portions of the contour or one or more of the external structural features may be more relevant to alignment with the optical axis and thus may be emphasized for formation in the recipient bed. In operation, the laser assembly (e.g., using a femtosecond laser) is programmed to create a recipient bed with stability and registration enhanced contour (e.g., positional spikes). The laser assembly can modify the implant to a substantially equivalent contour as the recipient bed and create a corneal flap or incision. The incision or flap is opened, the corneal implant is inserted so that the contours align, and the incision or flap is repositioned.

Feature registration refers to using a marker or other distinct feature of the implant for alignment with a feature of the eye (e.g., a pupil center position, an iris center position, an iris structure, and the like). For example, the corneal inlay can be formed with at least one distinct mark of known location on or within the inlay. An image of the recipient's eye is obtained (e.g., as displayed via the user interface 28, 60), and the intended location of the marker(s) on the corneal implant is determined (e.g., via treatment software in the system 10, 70). In one embodiment, image processing by the system 10, 70 determines the current location of the marker(s) and calculates an error signal for guiding the placement of the implant. The error signal can be represented on the user interface 28, 60 by overlays on the displayed image, although a variety of other techniques can be used (e.g., relative x-y coordinate values based on the optical axis, proximity indicators, and the like).

The corneal tissue implant is preferably selected to achieve a desired post-operative anterior corneal surface corresponding with a desired optical performance of the eye. As previously mentioned, non-optimal placement of the corneal implant can generate an error signal, for example, based on corneal topography, wavefront measurement, pachymetry, and the like. Using the error signal, the position of the implant is iteratively modified until the resulting error signal is substantially zero or within a pre-determined acceptable margin of error.

FIG. 3 is a cross-sectional view of a donor cornea 72 illustrating the formation of some corneal tissue inlays 78, 84, 86, 88, 90 in accordance with one embodiment. The donor cornea 72 has an epithelium 74 and an endothelium 76, among other structures (not shown). In this embodiment, multiple corneal tissue inlays 78, 84, 86, 88, 90 are incised (e.g., using the system 10, 70) from the donor cornea 72. The sequence or order of the inlays 78, 84, 86, 88, 90 as well as the type may be selected to maximize the number of inlays that may be incised and extracted from the donor cornea 72. A lens shaped lenticule 78, a planar shaped lenticule 88, a meniscus shaped lenticule 90, a larger ring shaped lenticule 84, and a smaller ring shaped lenticule 86 are incised from the donor cornea 72. Additional incisions 80 and 82 may be made in the donor cornea 72 to extract the various corneal tissue inlays 78, 88, and 90, and these incisions 80, 82 can form a cap or flap that may be lifted to reveal each respective inlay 78, 88, and 90.

FIG. 4 is a cross-sectional view of a recipient cornea 92 illustrating a pocket formation in accordance with one embodiment. The recipient cornea 92 has an epithelium 94 and an endothelium 96, among other structures (not shown). In this embodiment a lenticule (not shown) is incised and removed from the recipient cornea 92 to form a pocket 98, and an access 100 is incised to the pocket 98. The lenticule dimensions are preferably based on the refractive correction requirements for the recipient eye. A simple sub-surface incision may be made in place of incising the lenticule. The access 100 provides a conduit from the anterior surface of the cornea 92 to the pocket 98 for inserting the corneal tissue inlay.

FIG. 5 is a top view of a corneal tissue inlay 106 and a portion of an inserter 102 in accordance with one embodiment. FIG. 6 is a top view of the corneal tissue inlay 106 and the inserter 102 shown in FIG. 5 illustrating an insertion mode in accordance with one embodiment. The inserter 102 preferably has a non-stick surface and includes a handle 104 for user manipulation of the inserter 102. In one embodiment, the inserter 102 has shape memory and is biased in a rolled configuration, such as shown in FIG. 6. In another embodiment, a conventional intraocular lens inserter may be used with the corneal tissue inlay 106. Following formation of the corneal tissue inlay 106, the corneal tissue inlay 106 is placed on the inserter 102. In the insertion mode of this embodiment, the corneal tissue inlay 106 is rolled-up with a portion of the inserter 102 (e.g., a head) to have a narrow or slim configuration, which is useful for minimizing the dimensions of the access 100 (FIG. 4). A low-friction or non-stick coating can also be applied to one or more surfaces of the inlay 106. The inserter 102 may be manipulated through the access 100 to locate the corneal tissue inlay in the pocket 98 (FIG. 4), and the corneal tissue inlay 106 can be un-rolled within the pocket 98. The inserter 102 can then be extracted from the pocket 98. A probe, push-rod, or other simple device (not shown) may be used together with the inserter 102 to assist in depositing the corneal tissue inlay 106 within the pocket 98. In another embodiment, a flap is incised in the recipient cornea and lifted to reveal a corneal bed, the corneal tissue inlay 106 is deposited onto the corneal bed, and the flap is placed over the corneal tissue inlay 106.

Figure 7:
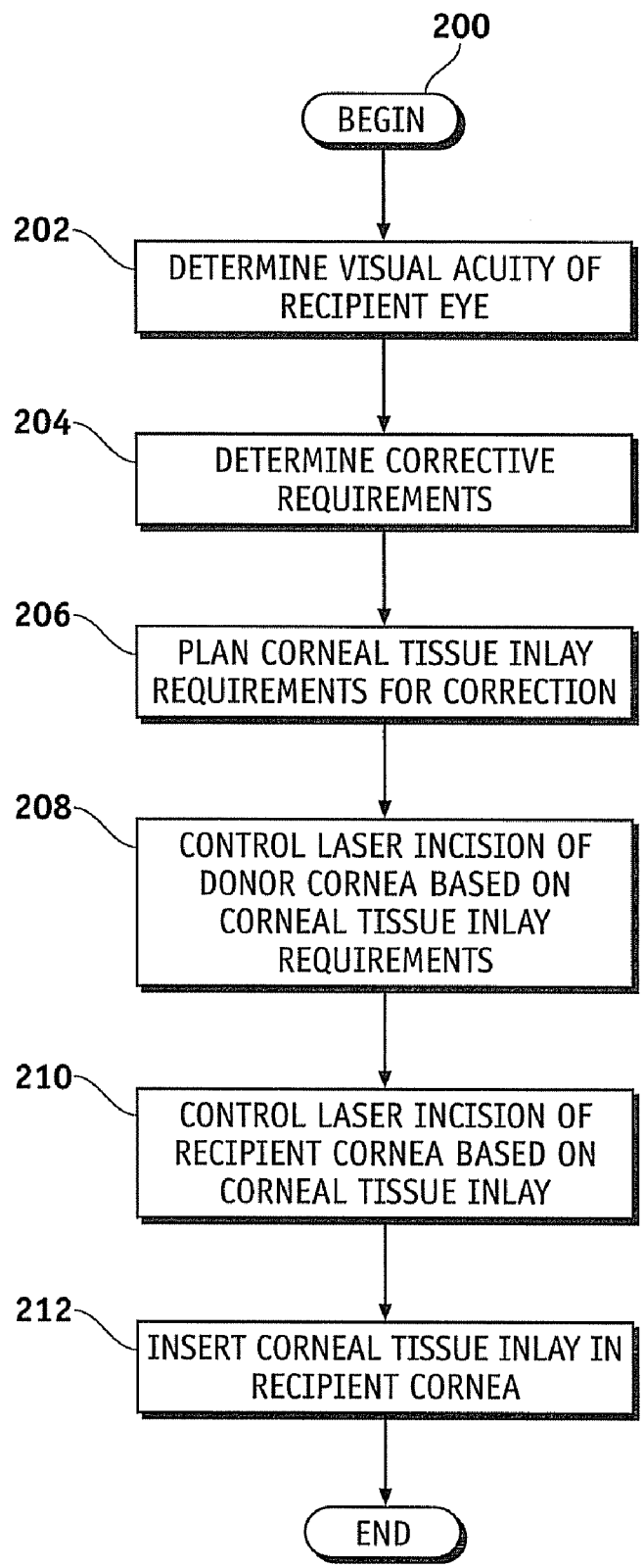
FIG. 7 is a flow diagram of a method for modifying a refractive profile of an eye in accordance with one embodiment.

FIG. 7 is a flow diagram of a method 200 for modifying a refractive profile of an eye in accordance with one embodiment. Visual acuity issues are determined for a recipient, as indicated at 202. For example, myopia, presbyopia, hyperopia, higher order aberrations, and the like, are determined for the recipient. Examples of devices to determine visual acuity issues include, but are not necessarily limited to, measurement devices such as Shack-Hartmann aberrometer, topographer, OCT, pachymeter, interferometry based devices, and other conventional visual acuity diagnostic devices. Additionally, pupilometry, iris registration, and/or residual accommodation may be used to determine visual acuity issues.

Corrective requirements are determined for the recipient, as indicated at 204. Some examples of corrections include, by way of example and not of limitation, refractive power change, multifocality, increase/decrease spherical aberration, higher order aberrations, and the like. Using the measurements for determining the visual acuity issues, modeling and/or designing a correction can be made based on corneal thickness, shape changes, or both. For example, the recipient cornea can be made thicker and more steeply curved to improve hyperopia. A central biconvex shaped corneal tissue inlay or plano-convex shaped corneal tissue inlay can increase the steepness of the cornea, whereas a ring-shaped corneal tissue inlay can flatten the cornea. In another example, a rigid, multifocal corneal tissue inlay can effect a multifocal cornea. In another example, the recipient cornea can be shaped to be more aspheric to enhance the depth of focus and/or reduce spherical aberration to improve visual acuity.

Corneal tissue inlay requirements for achieving the corrective requirements are planned, as indicated at 206. For example, a shape (e.g., biconvex, plano-convex, multifocal, aspheric, and the like) and physical dimensions (e.g., diameter, thickness, curvature, radii, profile, edge configuration, and the like) of the corneal tissue inlay are determined. Additionally, incision parameters of the recipient cornea may be planned. For example, an intrastromal pocket size and shape and an access incision may be determined for receiving the corneal tissue inlay. Pupil dynamics may also be accounted for in determining the corneal tissue inlay requirements.

Incisions in a donor cornea are controlled based on the corneal tissue inlay requirements, as indicated at 208. For example, an ophthalmic surgical laser (e.g., a femtosecond laser) is controlled to incise a lenticule from the donor cornea. The incisions may be pre-determined to produce a pocket that matches the corneal tissue inlay. In another embodiment, the incisions can be differently sized to create a different resulting recipient cornea shape (e.g., post implant or insertion of the corneal tissue inlay). The access incision can be limited to control egress of the corneal tissue inlay following insertion. Textured or shaped incisions may also be used to increase post-procedure healing and biomechanical strength of the recipient cornea. An axis associated with the access incision can be superiorly located to minimize gravity effects on the recipient cornea and/or to limit or correct astigmatism.

Incisions in a recipient cornea are controlled based on the incision parameters, as indicated at 210. For example, the ophthalmic surgical laser is controlled to incise the recipient cornea. The corneal tissue inlay is inserted into the recipient cornea, as indicated at 212, such as by manual manipulation with a blunt probe, forceps, or the like.

In one embodiment, the lenticule is sculpted or otherwise modified to impart one or more of the corneal tissue inlay requirements. For example, a femtosecond laser may be used to photoalter the anterior surface, the posterior surface, or a sub-surface layer of the lenticule. Additionally, the femtosecond laser may photoalter the edge of the lenticule to enhance the biomechanical stability of the corneal tissue inlay post-insertion. For example, the femtosecond laser may be used to produce a zig-zag edge. An excimer laser may also be used to photoalter one or both of the anterior and posterior surface of the lenticule (e.g., PRK). Fiducials, iris registration, pupil centration, or other orientation techniques may be used with the corneal tissue inlay for proper orientation of the corneal tissue inlay in the recipient cornea.

Thus, systems and methods of preparing a flap of a material with a pulsed laser beam are disclosed that improve the biomechanical integrity of material with the flap reintegrated therewith. In one embodiment, these systems and methods pro-actively enhance the healing of corneal flaps or corneal transplants. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A method of modifying a refractive profile associated with an eye having a recipient cornea, the method comprising the steps of:
   obtaining a corneal tissue inlay from a donor cornea, the corneal tissue inlay having a refractive profile, the obtaining step comprising:
      incising a portion of the donor cornea with a femtosecond laser, the portion having an anterior surface and a posterior surface, wherein the incising step comprises one of a group consisting of:
         incising one or more lenticules from the donor cornea with the femtosecond laser, the one or more lenticules selected from a group consisting of a biconvex lenticule, a plano-convex lenticule, a meniscus lenticule, and a ring-shaped lenticule;
         incising a sub-surface portion having a polygonal cross-section from the donor cornea with the femtosecond laser; and
         incising a sub-surface portion from the donor cornea with the femtosecond laser, the sub-surface portion having a perimeter selected from a group consisting of a round perimeter, an oval perimeter, and a polygonal perimeter;
      removing the sub-surface portion from the donor cornea; and
      sculpting at least one of the anterior surface and the posterior surface in conformance with the refractive profile of the corneal tissue inlay;
   forming a recipient bed in the recipient cornea; and
   positioning the corneal tissue inlay into the recipient bed to correct the refractive profile of the eye with the refractive profile of the corneal tissue inlay.

2. The method of claim 1, further comprising determining the refractive profile for the corneal tissue inlay based on the refractive profile of the eye prior to the step of positioning.

3. The method of claim 1, wherein the step of sculpting comprises photoaltering at least one of the anterior surface and the posterior surface with one of a femtosecond laser and an excimer laser.

4. The method of claim 1, wherein the step of incising comprises incising a lenticule from the donor cornea with the femtosecond laser.

5. The method of claim 1, wherein the step of obtaining further comprises incising an edge on the sub-surface portion, the edge configured to biomechanically stabilize a position of the corneal tissue inlay in the recipient bed.

6. The method of claim 1, wherein the step of forming comprises:
   incising a pocket in the recipient cornea, the recipient cornea having a surface, the pocket having the recipient bed and configured to receive the corneal tissue inlay; and
   incising a passage from the surface of the recipient cornea to the pocket.

7. The method of claim 1, wherein the eye has an optical axis, and wherein the step of forming comprises:
   forming the corneal tissue inlay and a recipient bed with matching contours;
   registering the corneal tissue inlay with the recipient bed to align the corneal tissue inlay with the optical axis and stabilize the corneal tissue inlay in the recipient bed;
   determining a position of the corneal tissue inlay;
   iteratively modifying the position of the corneal tissue inlay to align the refractive profile of the corneal tissue inlay with the refractive profile of the eye.

8. The method of claim 7, wherein the corneal tissue inlay has an orientation marker, and wherein the step of registering comprises:
   matching a contour of the corneal tissue inlay with a contour of the recipient bed; and
   aligning the orientation marker with a feature of the eye.

9. The method of claim 8, wherein the step of aligning comprises aligning the orientation marker with one or more of a pupil center position, an iris center position, and an iris structure.

10. The method of claim 1, further comprising orienting the corneal tissue inlay within the recipient bed based on at least one of an iris registration, a pupil-based centration, and pupil dynamics after the step of inserting.

11. The method of claim 1, wherein the step of obtaining comprises:
    removing the corneal tissue inlay from the donor cornea, the corneal tissue inlay having a surface;
    applying a non-stick film to the surface of the corneal tissue inlay; and
    collapsing the corneal tissue inlay.

12. The method of claim 1, further comprising photoaltering the recipient cornea with an excimer laser after the step of inserting.

13. The method of claim 1, wherein the corneal tissue inlay is a multifocal lenticule, and wherein the method further comprises altering a shape of the recipient cornea with the multifocal lenticule.

14. The method of claim 1, wherein the donor cornea is a cadaver cornea.

15. A system for modifying a refractive profile associated with an eye having a recipient cornea, the system comprising:
    a laser assembly operable to output a pulsed laser beam; and
    a controller coupled to the laser assembly and operable to direct the laser assembly to:
    incise a corneal tissue inlay from a donor cornea, the corneal tissue inlay having a refractive profile correcting for the refractive profile of the eye and having a contour;
    form a recipient bed in the recipient cornea, the recipient bed having a contour matching the contour of the corneal tissue inlay;
    register the corneal tissue inlay with the recipient bed;
    determine a position of the corneal tissue inlay; and
    determine a position change for the corneal tissue inlay based on the position of the corneal tissue inlay to align the refractive profile of the corneal tissue inlay with the refractive profile of the eye;
    wherein the controller is further configured to perform one of a group consisting of:
    direct the laser assembly to incise one or more lenticules from the donor cornea, the one or more lenticules having the refractive profile of the corneal tissue inlay and selected from a group consisting of a biconvex lenticule, a piano-convex lenticule, a meniscus lenticule, and a ring-shaped lenticule;
    direct the laser assembly to incise a sub-surface portion having a polygonal cross-section from the donor cornea, the sub-surface portion having the refractive profile of the corneal tissue inlay;
    direct the laser assembly to incise a sub-surface portion having a perimeter from the donor cornea, the sub-surface portion having the refractive profile of the corneal tissue inlay, the perimeter selected from a group consisting of a round perimeter, an oval perimeter, and a polygonal perimeter; and
    direct the laser assembly to incise an edge on the sub-surface portion, the edge configured to biomechanically stabilize a position of the corneal tissue inlay in the recipient bed.

16. The system of claim 15, wherein the controller is further configured to direct the laser assembly to:
    incise a portion of the donor cornea, the portion having an anterior surface and a posterior surface; and
    sculpt at least one of the anterior surface and the posterior surface in conformance with the refractive profile of the corneal tissue inlay.

17. The system of claim 15, wherein the controller is further configured to direct the laser assembly to:
    incise a pocket in the recipient cornea, the recipient cornea having a surface, the pocket having the recipient bed and configured to receive the corneal tissue inlay; and
    incise a passage from the surface of the recipient cornea to the pocket.

18. The system of claim 15, wherein the eye has an optical axis, and wherein the controller is further configured to align the corneal tissue inlay with the optical axis and stabilize the corneal tissue inlay in the recipient bed by registering the corneal tissue inlay with the recipient bed.

19. The system of claim 15, wherein the corneal tissue inlay has an orientation marker, and wherein the controller is further configured to determine an alignment of the orientation marker with one or more of a pupil center position, an iris center position, and an iris structure.

* * * * *